United States Patent [19]

Nyman

[11] 4,065,213

[45] Dec. 27, 1977

[54] APPARATUS FOR AND METHOD OF INSPECTING TUBULAR TEXTILE GOODS

[76] Inventor: Curt Lennart Nyman, Billdalsgaten 24, 502 64 Boras, Sweden

[21] Appl. No.: 707,755

[22] Filed: July 22, 1976

Related U.S. Application Data

[63] Continuation of Ser. No. 81,761, Oct. 19, 1970, abandoned.

[30] Foreign Application Priority Data

Oct. 22, 1969 Sweden .............................. 14443/69

[51] Int. Cl.² ............................................ G01N 21/16
[52] U.S. Cl. ..................................... 356/200; 356/238
[58] Field of Search ................ 356/200, 237, 238, 239

[56] References Cited

U.S. PATENT DOCUMENTS

| 1,015,730 | 1/1912 | Gill ................................... 356/236 X |
|---|---|---|
| 1,245,242 | 11/1917 | Kohn ............................... 356/238 X |
| 1,728,458 | 9/1929 | Verduce .............................. 356/238 |
| 2,059,308 | 11/1936 | Boadwee et al. .................... 356/238 |
| 2,502,469 | 4/1950 | Martin ................................ 356/237 |
| 2,900,512 | 8/1959 | Jolly .................................. 356/238 X |
| 3,474,254 | 10/1969 | Piepenbrink et al. ............ 356/238 X |
| 3,554,656 | 1/1971 | Eicken .............................. 356/238 |
| 3,556,665 | 1/1971 | Hertel ............................... 356/238 |

FOREIGN PATENT DOCUMENTS

| 6,600,549 | 1/1967 | Netherlands ......................... 356/238 |
|---|---|---|
| 928,405 | 6/1963 | United Kingdom ................. 356/238 |
| 841,409 | 7/1960 | United Kingdom ................... 356/24 |

Primary Examiner—F. L. Evans
Attorney, Agent, or Firm—Robert E. Burns; Emmanuel J. Lobato; Bruce L. Adams

[57] ABSTRACT

An apparatus of the type including a guide for guiding longitudinally advancing tubular textile goods, and a member disposed within the advancing tubular textile goods for flattening a portion of the advancing tubular textile goods into a flattened portion having a pair of major opposed sides which jointly comprise the entire surface area of the flattened portion of the tubular textile goods. The guide is comprised of a pair of opposed rollers defining therebetween an elongated narrow slot or nip for receiving the advancing tubular textile goods in the flattened configuration. The member for flattening the advancing tubular textile goods comprises a plate-like member which is disposed in use within the tubular textile goods above the pair of opposed rollers. A method of inspecting tubular textile goods comprises advancing the tubular textile goods over a plate-like member so that they are stretched flat as they pass over the plate-like member, passing the flattened tubular textile goods through a narrow slot which is dimensioned to pass the same but which is too narrow to pass the plate-like member, and simultaneously inspecting both sides of the flattened portion of the advancing tubular textile goods in order to inspect the entire surface area thereof.

17 Claims, 7 Drawing Figures

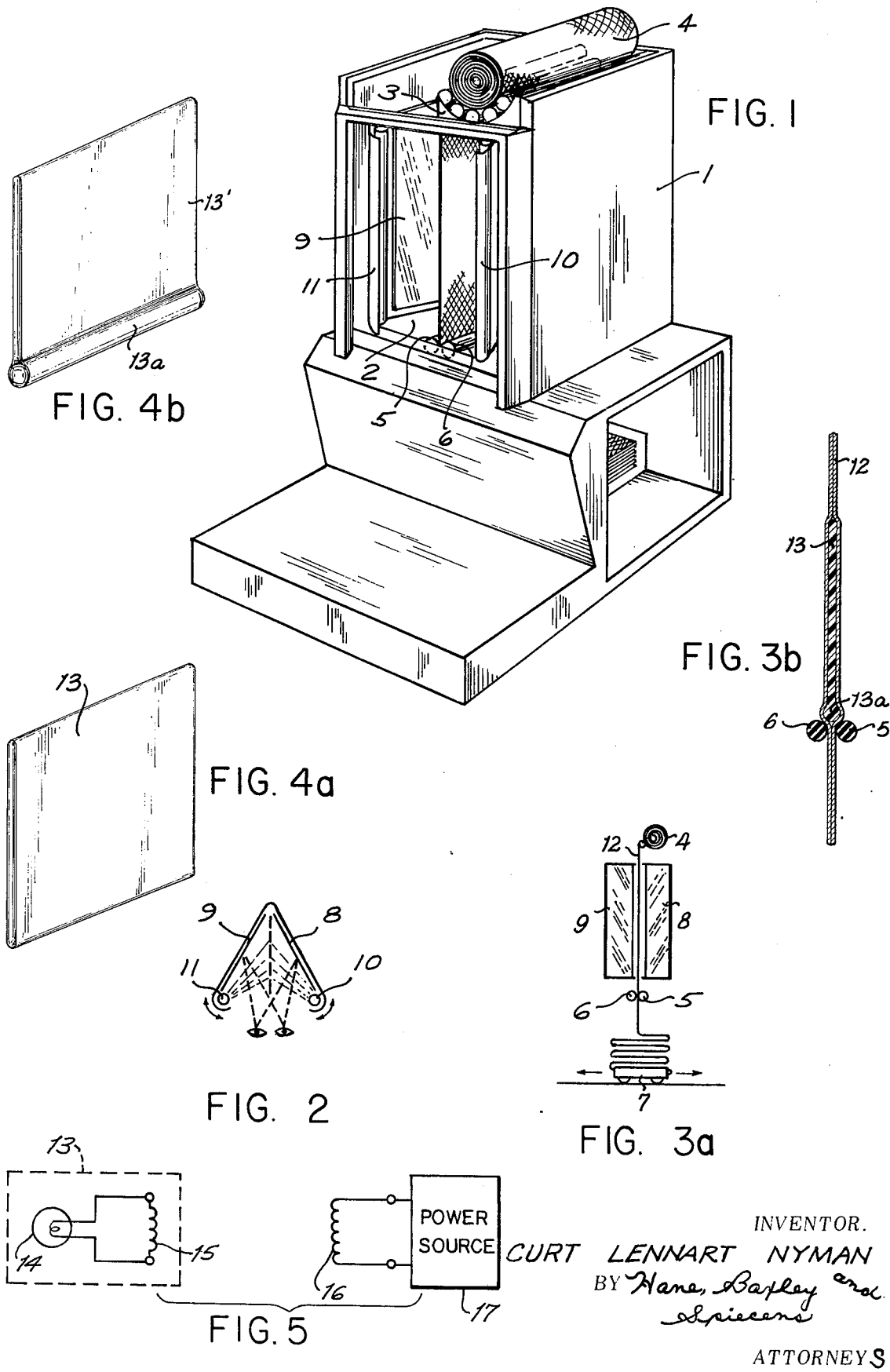

APPARATUS FOR AND METHOD OF INSPECTING TUBULAR TEXTILE GOODS

This is a Continuation Application of prior U.S. application Ser. No. 81,761, filed Oct. 19, 1970 and now abandoned.

BACKGROUND OF THE INVENTION

The present invention relates to an apparatus for inspecting tubular textile goods, and to a method for inspecting tubular textile goods. More particularly, the present invention relates to an apparatus for and method of inspecting tubular textile goods by simultaneously inspecting the entire surface area of a portion defined along the length of the tubular textile goods while they are being longitudinally advanced so that inspection can be completely carried out with one pass of the tubular textile goods past an observer.

Modern high speed textile machines produce tubular textile goods, including both knitted goods and woven goods. These tubular textile goods are handle by rolling them up in a flattened web-like condition. When rolled up, the tubular textile goods are similar to an elongated web of material comprised of two layers or two plies.

Various methods of inspecting tubular textile goods after they have been rolled up in a flattened web-like configuration are known. According to one method the roll is placed in a cradle which is positioned at the upper end of an inclined table. The textile goods are then unrolled and advanced in a flattened configuration down the inclined table and are collected at the lower end of the table and stacked in a zig-zag or fan folded configuration. As the textile goods pass along the table the upper side of the textile goods are inspected by an observer, or are sensed by a camera that transmits signals to an appropriate control member for controlling the advancing of the flattened textile goods along the table.

When all of the textile goods have been unrolled, advanced along the table and inspected, and stacked the stack of folded textile goods is then placed in the cradle and the textile goods are again advanced along the table for inspection. This time, however, the opposite side of the flattened textile goods faces the observer so that the entire surface area of the textile goods is inspected.

The previously described method requires that the textile goods pass by the observer twice so that the entire surface area of the flattened textile goods can be inspected. If the entire surface of the textile goods could be inspected with a single pass of the textile goods by the observer the rate at which the the textile goods could be inspected would be substantially increased with an attendant decrease in the cost of inspection. Moreover, the inspection would be more thorough if the two layers of the flattened textile goods could be separated by a member having a colour contrasting with the colour of the textile goods. With the flattened textile goods comprising two layers, a flaw in the upper layer being observed may be difficult to detect because the lower layer has the same colour as the upper layer. A member having a colour contrasting with that of the flattened textile goods and disposed between the two layers would enhance the visibility of flaws and permit a more thorough inspection.

An apparatus which partially solves the problem of eliminating the requirement for two passes of the flattened textile goods in order to completely inspect the same is disclosed in British Pat. No. 928,405 which discloses "Improvements in or relating to the inspection of circular-knitted fabric". The disclosed apparatus includes a frame with an arbor for carrying a roll of tubular textile goods wound thereon in a flattened web-like configuration. Guide rollers mounted on the frame guide the textile goods, which remain in a web-like configuration, to a pair of opposed driven draw rollers. The flattened textile goods pass between the pair of draw rollers which are driven to longitudinally advance the flattened textile goods and unroll them. The apparatus further comprises a casing position along the path of advance of the flattened textile goods and supported on a pair of columns. The flattened textile goods pass over the casing before they reach the pair of opposed draw rollers. The casing is transparent and houses flourescent lamps which illuminate the flattened textile goods from within to enhance the visibility of flaws. Moreover, by using a mirror positioned relative to the casing it is possible for a single observer to simultaneously inspect both sides of the flattened textile goods as they pass over the casing and therefore eliminate the requirement of more than one pass of the flattened textile goods by the observer in order to completely inspect the entire surface of the flattened textile goods.

In the patented apparatus the casing is supported by a pair of columns which extend from the frame up to the casing and which extend along a path of advance of the textile goods. Therefore, after the flattened textile goods have passed over the casing and between the draw rollers they pass over and completely surround the columns supporting the casing. Consequently, to remove the textile goods from the apparatus after inspection has been completed it is necessary to advance the textile goods in the opposite direction from which they were previously advanced to pass them back between the pair of draw rollers and over the casing. Although an observer does not have to continually watch the textile goods as they are being advanced in the reverse direction so that the textile goods can be advanced in the reverse direction at a higher speed than that at which they were advanced during inspection, an operator must still attend to this operation and it is time consuming. The elimination of the requirement to advance the textile goods in the reverse direction before they can be removed from the inspection apparatus would result in further savings of time and money and would therefore be very desirable.

SUMMARY OF THE INVENTION

It is a primary object of the present invention to provide an apparatus for use in the inspection of tubular textile goods which permits the entire surface of the tubular textile goods to be inspected during a single pass past an observer, and which thereafter permits the inspected tubular textile goods to be removed from the apparatus without any further operations.

Another object of the invention is to provide an apparatus for use in the inspection of tubular textile goods which includes a member disposed within the tubular textile goods during the inspection thereof and which has a colour contrasting to the colour of the tubular textile goods to facilitate the visual detection of flaws in the textile goods. Another object of the present invention is to provide an apparatus for use in the inspection of tubular textile goods which includes means for illuminating the tubular textile goods from within while they are being inspected in order to facilitate visual detection of flaws in the textile goods. Still another object of the invention is to provide a method for inspecting tubular textile goods which permits the entire area of the textile goods to be inspected during a single pass of the textile goods past an observer, and which thereafter does not require any further steps for the recovery of the textile goods.

Another object of the present invention is to provide a method of inspecting tubular textile goods which permits inspection of the entire area of the textile goods during a single pass of the textile goods past an observer and while the textile goods pass over a member having a colour contrasting to that of the textile goods to enhance visibility of flaws. Still another object of the invention is to provide a method of inspecting tubular textile goods which permits inspection of the entire area of the textile goods during a single pass of the textile goods past an observer and while the tubular textile goods are being illuminated from within to enhance visibility of flaws.

An apparatus according to the invention comprises means for guiding longitudinally advancing tubular textile goods along a path of travel, and means disposed within the longitudinally advancing tubular textile goods for flattening a portion of the same into a web-like configuration having a pair of major opposed spaced sides which jointly comprise the entire surface area of the flattened portion of the advancing tubular textile goods. The means for guiding comprises means defining an elongated narrow slot for receiving the longitudinally advancing tubular textile goods in the flattened web-like configuration. The means for flattening a portion of the longitudinally advancing tubular textile goods comprises a plate-like member disposed within the tubular textile goods and dimensioned to stretch a portion of the textile goods to form the flattened portion thereof. The plate-like member is disposed in use within the tubular textile goods and above the means defining an elongated narrow slot to flatten a portion of the tubular textile goods as they progressively advance over the plate-like member and through the narrow elongated slot so that the entire surface area of the flattened portion of the advancing tubular textile goods may be inspected by simultaneously inspecting both sides of the flattened portion of the textile goods.

The means for guiding comprises a pair of opposed rollers having a nip therebetween which nip constitutes the narrow elongated slot. The plate-like member is disposed in use within the tubular textile goods above the pair of opposed rollers with the textile goods passing over the plate-like member and through the nip between the pair of opposed rollers. In one embodiment the plate-like member includes an edge portion thicker than a major portion of the plate-like member and thicker than a width of the narrow elongated slot. The thick edge portion of the plate-like member prevents the plate-like member from sliding through the narrow elongated slot. The plate-like member is coloured and has a colour which contrasts with the colour of the tubular textile goods. Alternatively, the plate-like member comprises illuminating means energizable for illuminating the textile goods from within as they pass over the plate-like member, and the apparatus according to the invention further comprises means for energizing the illuminating means.

The method of inspecting tubular textile goods according to the invention comprises advancing the tubular textile goods over a plate-like member having a width dimension sufficiently great so that the advancing textile goods are stretched flat as they pass over the plate-like member, passing the advancing tubular textile goods through a narrow slot dimensioned to pass the tubular textile goods in a flattened configuration but too narrow to pass the plate-like member, and simultaneously inspecting the flattened portion of the advancing tubular textile goods on both sides of the plate-like member. The method according to the invention is carried out with the plate-like member comprising means for illuminating the flattened portion of the advancing tubular textile goods from within. Alternatively, the method is carried out with a plate-like member which has a colour that constrasts with the colour of the tubular textile goods to enhance visibility of flaws in the textile goods as they pass over the coloured plate-like member.

BRIEF DESCRIPTION OF THE DRAWINGS

Other features and advantages of the apparatus for use in the inspection of tubular textile goods and method of inspecting tubular textile goods according to the invention will be apparent from the disclosure and from the appended claims and drawings in which:

FIG. 1 is a perspective view of the apparatus according to the invention;

FIG. 2 is a plane view showing the relationship between the textile goods in a flattened configuration and a pair of mirrors for simultaneously projecting images of both sides of the flattened textile goods to a single observer;

FIG. 3a is a vertical elevation showing the relative position of the flattened textile goods and the pair of mirrors illustrated in FIG. 2;

FIG. 3b is a vertical section of the flattened portion of the tubular textile goods with a plate-like member disposed therein;

FIGS. 4a and 4b illustrate different embodiments of the platelike member; and

FIG. 5 is a schematic circuit diagram of the illuminating means of the invention.

DESCRIPTION OF THE PREFERRED EMBODIMENTS

The apparatus for use in the inspection of tubular textile goods according to the invention illustrated in the drawings comprises a housing 1 having a viewing aperture 2. The housing further includes a cradle 3 for receiving in use a roll 4 of tubular textile goods rolled in a flattened web-like configuration. The flattened textile goods extend down from the cradle 3 past the viewing aperture 2 and between a pair of opposed rollers 5,6. The rollers 5, 6 are preferably mounted for rotation and have therebetween a nip which constitutes a narrow elongated slot for receiving and passing therethrough the textile goods in the flattened configuration. The pair of rollers 5,6 jointly comprise means for guiding the textile goods as they are unwound from the roll 4 and advanced in a longitudinal direction thereof past the viewing aperture 2 and through the open elongated narrow slot defined between the pair of rollers 5, 6. As shown in the FIGS. the slot is unobstructed by any structural elements of the apparatus. Although the means for guiding the advancing flattened textile goods is illustrated as being comprised of the rollers 5,6 it must be understood that the slot between the pair of rollers can be defined by any other suitable structure and the invention is not limited to apparatus having a pair of rollers defining a narrow elongated slot.

Disposed within the housing 1 and opposite the viewing aperture 2 is a pair of planar mirrors 8,9. Each of these mirrors is disposed opposite a respective side of the flattened textile goods as can be seen in FIGS. 2 and 3a. The textile goods extending from the roll 4 between the mirrors 8,9 and through the slot between the rollers 5,6 is a flattened web-like portion 12. The mirrors 8,9 are positioned relative to the flattened portion 12 of the textile goods so that they project images of both sides of the flattened portion 12 of the textile goods to a single observer positioned opposite the viewing aperture 2. As the textile goods are longitudinally advanced the portion of the textile goods opposite the viewing aperture 2 may be continually observed and both sides of the flattened portion 12 of the textile goods may be continually simultaneously inspected so that the entire surface of the textile goods can be inspected during a single pass of the textile goods past the viewing aperture 2.

As shown in FIG. 2, the mirrors 8, 9 are positioned opposite each other and converge in a direction away from the viewing aperture 2 and diverge in a direction toward the viewing aperture 2, so that the mirrors 8, 9 form an acute angle therebetween. Lamps 10, 11 are disposed adjacent respective ones of the mirrors 8, 9 and at the edges of the mirrors which are adjacent the viewing aperture 2. The lamps may be tubular flourescent lamps positioned vertically for illuminating the opposite sides of the flattened portion 12 of the textile goods opposite the viewing aperture 2. Consequently, the surfaces of the flattened portion 12 of the textile goods will be well illuminated and the mirrors will project bright images of the opposite sides of the flattened portion 12 of the textile goods to permit an observer stationed opposite the viewing aperture 2 to detect flaws in the textile goods as they advance past the viewing aperture 2.

After the textile goods pass through the slot defined between the roller 5, 6 they are stacked on a reciprocating car or carriage 7. The reciprocal movement of the car 7 causes the advancing textile goods to stack in a zig-zag or fan-folded configuration. After inspection of the textile goods is complete the stacked fan-folded textile goods can simply be removed from the car 7, a new roll 4 of textile goods placed in the cradle 3, and the inspection operation is again ready to commence.

The flattened portion 12 of the textile goods is maintained in the flattened web-like configuration by a plate-like member 13 disposed within the textile goods. The plate-like member 13 is illustrated in FIG. 4a and has a generally rectangular configuration and is sufficiently wide to stretch the textile goods flat to form the flattened portion 12 as the textile goods advance over it. The height of the plate-like member 13 is generally on the order of the distance between the slot defined between rollers 5, 6 and the cradle 3.

The plate-like member 13 is sufficiently thick to prevent it from sliding through the slot defined between the rollers 5, 6, and as shown in FIG. 4a it may have a uniform thickness. An alternative embodiment is the plate-like member 13' illustrated in FIG. 4b. The plate-like member 13' includes a thick edge portion 13'a which is thicker than the rest of the plate-like member 13'. The thick edge portion 13'a is sufficiently wide to prevent the plate-like member 13' from sliding through the slot between the rollers 5, 6.

FIG. 3b is a sectional view of the plate-like member 13' disposed within the textile goods and positioned above and supported by the pair of opposed rollers 5, 6.

The two sides of the flattened portion 12 of the textile goods are on opposite sides of the plate-like member 13' and extend downward over the sides of the plate-like member 13'. The textile goods then pass over the thick edge portion 13'a and thereafter converge and pass through the slot between the pair of rollers 5, 6. As shown in FIG. 3b the width of the thick edge portion 13'a is sufficient to prevent the plate-like member 13' from sliding through the slot between the pair of rollers 5, 6. The plate-like member 13' and the thick edge portion 13'a are illustrated as comprising a unitary structure. However, the thick edge portion 13'a may be provided by mounting a bar or a roller along an edge of the platelike member. In this case, the roller can be mounted on bearings for rotation.

The plate-like member preferably is coloured and has a colour which contrasts with the colour of the textile goods. Consequently, as the advancing textile goods pass over the plate-like member 13 flaws or defects will be more noticeable than if the colour of the plate-like member 13 and the textile goods do not contrast.

In another embodiment of the apparatus according to the invention the plate-like member 13 includes illuminating means for illuminating the flattened portion 12 of the textile goods from within. The illuminating means is illustrated schematically in FIG. 5 and jointly comprises a lamp 14 and a coil 15 connected to the lamp. The lamp 14 and coil 15 are positioned within the plate-like member 13 so that when the lamp 14 is energized it will illuminate the flattened portion 12 of the textile goods from within. Means for energizing the coil is also illustrated in FIG. 5 and jointly comprises a second coil 16 and a power source 17 connected to the second coil 16. The two coils 15, 16 are inductively coupled so that power supplied to the coil 16 will be transferred by induction to the coil 15 thereby to develop currents in coil 15 and energize the lamp 14. The coil 15 defines means energizable by induction for energizing the lamp 14. The light from the lamp 14 enhances the visibility of flaws in the textile goods as the textile goods pass over the plate-like member 13 so that internal illumination of the flattened portion 12 of the textile goods facilitates inspection. More than one lamp may be provided within the plate-like member 13, depending upon the required degree of illumination.

The method of inspecting tubular textile goods according to the invention is carried out by advancing the tubular textile goods over the plate-like member 13 in order to stretch the textile goods flat as they pass over the plate-like member 13. The textile goods are advanced over the plate-like member 13 and then through the narrow slot between the rollers 5, 6 which slot is dimensioned to pass tubular textile goods in a flattened configuration but which is too narrow to pass the plate-like member. As the advancing textile goods pass over the plate-like member 13 the entire surface of the textile goods on both sides of the plate-like member is simultaneously inspected so that the entire surface of the tubular textile goods is inspected during one pass of the textile goods over the plate-like member 13. The method according to the invention is preferably carried out with a plate-like member including means for illuminating the textile goods from within as they pass thereover. Alternatively, the method is carried out with a plate-like member 13 which is coloured and has a colour which contrasts with a colour of the textile goods.

The above described embodiments of the invention are illustrative only and are not limitive of the scope of the invention. For example, the arrangement of mirrors for simultaneously reflecting images of both sides of the flattened portion of the textile goods to a single observer may be any arrangement which carries out the desired function and need not consist of the pair of mirrors shown. Moreover, the plate-like member 13 need not be flat as shown. The opposed major surfaces of the plate-like member can be arced or curved. Moreover, the textile goods need not advance downward from the cradle to the pair of opposed rollers. Instead, the roll of textile goods to be inspected could be mounted beneath the pair of opposed rollers and the textile goods could advance upwardly past the viewing aperture to a take-up roll positioned where the cradle is shown. These and other modifications of the described embodiments are within the scope of the invention as set forth in the following claims.

I claim:

1. In an apparatus, for use in the inspection of tubular textile goods, of the type including means for guiding longitudinally advancing tubular textile goods along a path of travel, and means disposed within the longitudinally advancing tubular textile goods for flattening a portion of the longitudinally advancing tubular textile goods into a web-like configuration having a pair of major opposed spaced sides jointly comprising the entire surface area of the flattened portion of the advancing tubular textile goods in order to permit simultaneous inspection of substantially the entire surface of the advancing tubular textile goods as they advance by simultaneously inspecting the pair of major opposed sides of the flattened portion of the advancing tubular textile goods, the improvement which comprises:

said means for guiding comprising means defining an open elongated narrow slot unobstructed by any structural elements of the apparatus for receiving the longitudinally advancing tubular textile goods in the flattened web-like configuration; and said means for flattening a portion of the longitudinally advancing tubular textile goods comprising a plate-like member disposed within the tubular textile goods and dimensioned to stretch a portion of the tubular textile goods to form the flattened portion of the same and said plate-like member being sufficiently thick to prevent its passage through the slot, said plate-like member being disposed in use within the tubular textile goods above and supported by said means defining an open elongated narrow slot to flatten a portion of the tubular textile goods as they progressively longitudinally advance over said plate-like member and through said open narrow elongated slot, said tubular textile goods conforming to the shape of the plate-like member as they advance whereby the flattened portion of the tubular textile goods is formed above said means defining an open elongated narrow slot and the major opposed sides of the flattened portion converging as the tubular textile goods advance into the open elongated slot and pass between said plate-like member and said means defining an elongated slot whereby said plate-like member forms the flattened portion of the advancing tubular textile goods while being supported by said means defining an open elongated narrow slot and is maintained positioned above the slot by the advancing tubular textile goods.

2. In an apparatus for inspecting tubular textile goods according to claim 1:

wherein said means for guiding comprise a pair of opposed rollers having anip therebetween which nip consitututes said narrow elongated slot; and wherein said plate-like member is disposed in use within the tubular textile goods above said pair of opposed rollers with the tubular textile goods passing over said plate-like member and through the nip between said pair of opposed rollers.

3. In an apparatus for inspecting tubular textile goods according to claim 1, wherein said plate-like member includes a thick edge portion thicker than a major portion thereof and thicker than a width of said narrow elongated slot, said plate-like member being disposed in use within said tubular textile goods opposite said narrow elongated slot, whereby the thick edge portion of said plate-like member prevents said plate-like member from sliding through the narrow elongated slot.

4. In an apparatus for inspecting tubular textile goods according to claim 1, wherein said plate-like member is coloured and has a colour which contrasts with a colour of the tubular textile goods to enhance visibility of flaws in the tubular textile goods as they pass over the coloured plate-like member.

5. In an apparatus for inspecting tubular textile goods according to claim 1, wherein said plate-like member comprises illuminating means energizable for illuminating said tubular textile goods from within to enhance the visability of flaws in the tubular textile goods which pass over said plate-like member, and wherein the apparatus further comprises means for energizing said illuminating means.

6. In an apparatus for inspecting tubular textile goods according to claim 1, further comprising: projecting means for projecting the images of both sides of the flattened portion of the advancing tubular textile goods to an observer to allow the observer to simulataneously observe both sides of the flattened portion of the advancing tubular textile goods.

7. In an apparatus for inspecting tubular textile goods according to claim 6, wherein said projecting means comprise a pair of planar mirrors each having a reflective surface and disposed with their respective reflective surfaces facing each other and with the mirrors forming an acute angle there between, said pair of mirrors being positioned with a respective one of the mirrors opposite a different side of the flat portion of said tubular textile goods, and said pair of mirrors being positioned relative to the flat portion of the tubular textile goods to project images of both sides of the flat portion of the tubular goods to an observer position, whereby a single observer can simultaneously observe both sides of the flattened portion of the advancing tubular textile goods.

8. In an apparatus for inspecting tubular textile goods according to claim 5, wherein said illuminating means comprised by said plate-like member includes a lamp and means energizable by induction for energizing said lamp.

9. An apparatus, for inspecting advancing tubular textile goods, comprising in combination:

support means for supporting tubular textile goods to be inspected in the form of a rolled-up web having two adjacent sides:

means for collecting the tubular textile goods after inspection thereof;

a frame structure including an inspection aperture, said support means being disposed on the frame above the inspection aperture for feeding the web past the inspection aperture toward the means for collecting disposed below the inspection aperture;

guide means for guiding the goods past the inspection aperture and disposed on said frame, said guide means defining a passage for guiding the web to the means for collecting;

means comprising a plate freely interposed between he sides of the web to effect separation of the sides as the web passes past the inspection aperture, said plate having a substantially rectangular configuration and a width approximately matching the width of the web for flattening the web sides upon opposite sides of the plate at least the end of the plate facing the guide means being of sufficient thickness so as to prevent sliding of the plate through the passage in the guide means;

means for simultaneously illuminating the web portion moving over both sides of the plate; and projection means for simultaneously projecting images of both web sides moving over the sides of the plate to a viewing position.

10. The apparatus of claim 9 wherein said projecting means comprise two planar mirrors mutually oriented at an oblique angle and partially encompassing the goods moving over said plate.

11. The apparatus of claim 9 wherein said plate has a colour which constrasts with the colour of the tubular textile goods.

12. The apparatus of claim 9 wherein said plate includes illuminating means inductively energizable for illuminating the web.

13. The apparatus according to claim 9 wherein said plate includes at the end facing the guide means an enlarged rounded portion extending across the width of the plate.

14. A method of inspecting tubular textile goods, comprising:

advancing tubular textile goods over a plate-like member having a width dimension sufficiently great so that the advancing tubular textile goods are stretched flat as they pass over the plate-like member;

passing the advancing tubular textile goods through an open unobstructed narrow slot, dimensioned to pass the tubular textile goods in a flattened configuration but too narrow to pass the plate-like member, after the tubular textile goods have passed over the plate-like member with the plate-like member adjacent the slot and prevented by the slot from advancing along with the tubular textile goods thereby to maintain the platelike member at a fixed position; and simultaneously inspecting the flattened portion of the advancing tubular textile goods on both sides of the plate-like member.

15. A method of inspecting tubular textile goods according to claim 14, wherein said plate-like member includes means for illuminating the flattened portion of the advancing tubular textile goods from within, and wherein the step of simultaneously inspecting both sides of the flattened portion of the advancing tubular textile goods is carried out while the flattened portion of the advancing tubular textile goods is illuminated from within.

16. A method of inspecting tubular textile goods according to claim 14, wherein said plate-like member has a colour which contrasts with a colour of the tubular textile goods to enhance visability of flaws in the tubular textile goods as they pass over the coloured plate-like member.

17. In a method of inspecting tubular textile goods according to claim 15, wherein said illuminating means comprised by said plate-like member includes a lamp and means energizable by induction for energizing said lamp.

* * * * *